United States Patent [19]

Hoge

[11] 4,321,328
[45] Mar. 23, 1982

[54] PROCESS FOR MAKING ETHANOL AND FUEL PRODUCT

[76] Inventor: William H. Hoge, R.D. 2, Tuccamirgan Rd., Flemington, N.J. 08822

[21] Appl. No.: 213,363

[22] Filed: Dec. 5, 1980

[51] Int. Cl.³ .............................................. C12P 7/10
[52] U.S. Cl. .................................. 435/165; 435/161; 435/162
[58] Field of Search ............... 435/161, 162, 163, 164, 435/165, 813

[56] References Cited

U.S. PATENT DOCUMENTS

| | | |
|---|---|---|
| 1,323,540 | 12/1919 | Moore . |
| 2,802,774 | 8/1957 | Griesbach ............................ 195/15 |
| 3,642,580 | 2/1972 | Ghose et al. ....................... 195/33 R |
| 3,764,475 | 10/1973 | Mandels et al. ................... 195/33 R |
| 3,972,775 | 8/1976 | Wilke et al. ........................ 195/33 |
| 3,990,944 | 11/1976 | Gauss et al. ........................ 195/33 |
| 4,009,075 | 2/1977 | Hoge .................................... 195/33 |
| 4,094,742 | 6/1978 | Bellamy .............................. 195/33 |
| 4,201,596 | 5/1980 | Church et al. ...................... 127/37 |
| 4,287,304 | 9/1981 | Muller et al. ....................... 435/161 |

OTHER PUBLICATIONS

O. C. Sitton et al., "Ethanol from Agricultural Residues", Chemical Engg. Progress, Dec. 1979, pp. 52–57.
M. C. Flickinger, "Current Biological Research in Conversion of Cellulosic Carbohydrates into Liquid Fuels: How Far Have We Come?", Biotechnology and Bioengineering, vol. XXII, Suppl. 1, 27–48 (1980).
P. J. Blotkamp et al., "Enzymatic Hydrolysis of Cellulose and Simultaneous Fermentation into Alcohol", A.I.Ch.E. Symp. Series vol. 74, No. 181, pp. 85–90, (1978).

Primary Examiner—Raymond N. Jones
Assistant Examiner—John E. Tarcza
Attorney, Agent, or Firm—Folsom E. Drummond

[57] ABSTRACT

A process for the production of ethanol, useful as a fuel, from various cellulose-containing materials by saccharification, fermentation and distillation of the resultant fermented ethanol-containing beer to recover ethanol; which comprises the formation of a slurry of the material being saccharified by recycling a portion of the resultant fermented ethanol-containing beer back to the incoming material being subjected to saccharification whereby the concentration of ethanol during fermentation and subsequent distillation treatment is substantially increased over that utilizing no recycling treatment, the process being carried out at under normal atmospheric conditions.

8 Claims, 1 Drawing Figure

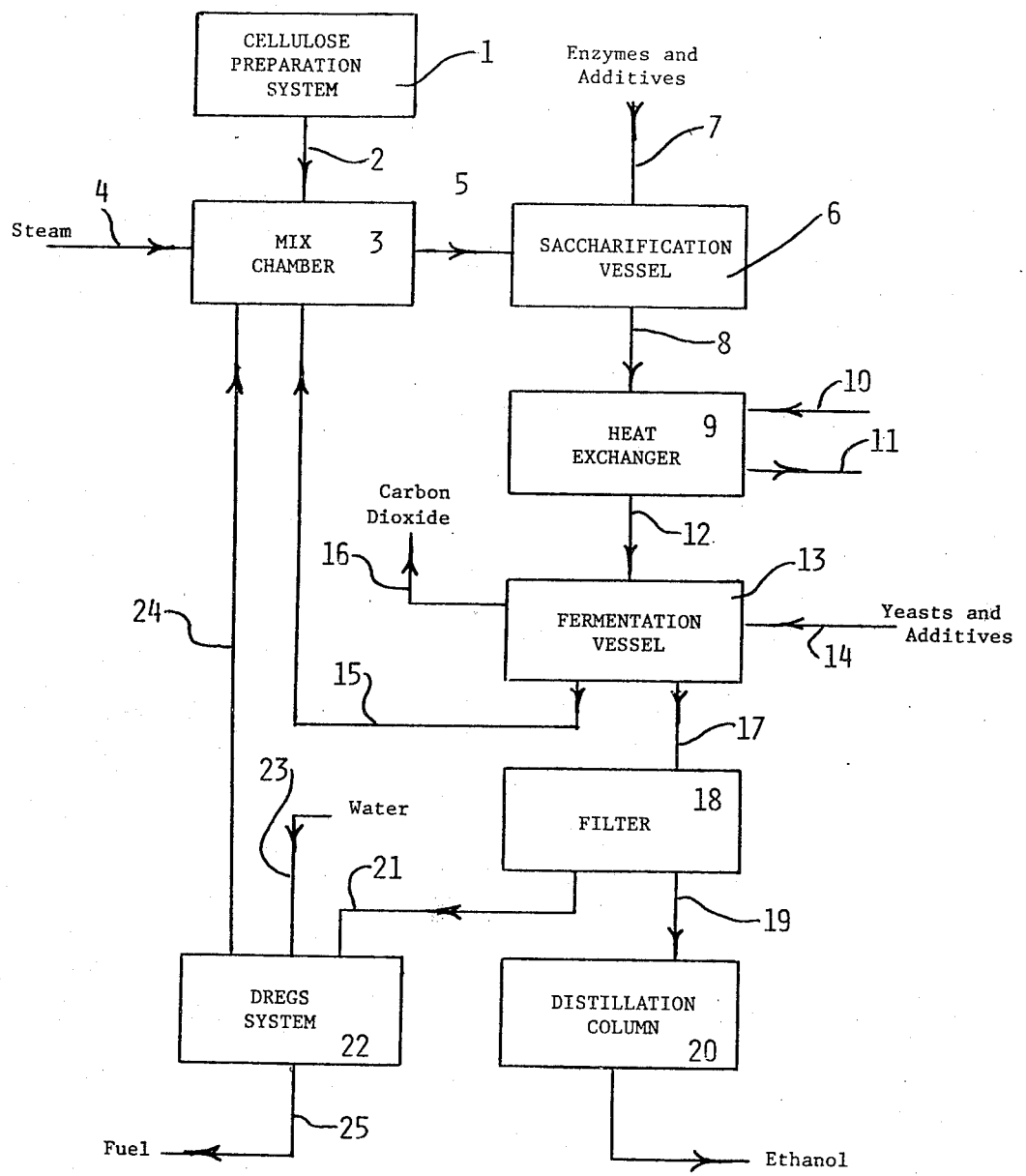

PROCESS FOR MAKING ETHANOL AND FUEL PRODUCT

BACKGROUND OF THE INVENTION

The manufacture of ethanol from cellulose-containing materials has been known for many years. Two reactions are needed. The first is the hydrolysis of cellulose into fermentable sugars, and this reaction is also referred to as "saccharification". The second reaction involves the conversion of the sugars to ethanol, and this is commonly done by a fermentation with yeast.

The saccharification can be accomplished by addition of acids, as described in the U.S. Pat. Nos. of Moore, 1,323,540, and in the patent of Church et al, 4,201,596. The saccharification can also be accomplished by cellulases, as described in the patent of Mandels et al, 3,764,475, and in the patent of Ghose, 3,642,580. Additional agents for microbiological saccharification include thermophilic cellulolytic sporocytophaga, as described in the patent of Bellamy, 4,094,742.

The formation of ethanol from the sugars can be accomplished by yeasts such as *Saccharomyces cerevisiae*, described in the patent of Griesbach, 2,802,774, and *Fusarium oxysporum*, as referred to in the article by Sitton et al on page 52 of the December 1979 issue of Chemical Engineering Progress. Other useful microorganisms are the ethanol-producing bacillus described by Bellamy in U.S. Pat. No. 4,094,742. Additional promising microorganisms for either the saccharification or fermentation are listed by Flickinger, Biotechnology and Bioengineering, Vol. XXI, Suppl. 1, 27–48 (1980).

The commercial manufacture of ethanol from cellulose has lagged because of several major process problems involving saccharification, the reactivity of the raw materials and the energy required to purify the ethanol.

Saccharification has been a problem because acid saccharification is troubled by corrosion problems, by problems in recovering the acid, and from the formation of non-fermentable compounds from the high-temperature reaction between the acid and the sugars. Saccharification by enzyme has been uneconomical because of the slow reaction of the enzyme, by the high cost of the enzyme and by the inhibiting effect of the sugars on the reaction rate.

Reactivity of the cellulose-containing raw materials has been a problem. In practice, it is usually possible to only get about 20 pounds of ethanol from 100 pounds of dry wood or the like cellulosic material. The unreactive fraction of wood, for example, is usually over 50% of the initial weight. The ethanol yields can be greatly increased by starting with a purified cellulose or a precipitated amorphous cellulose. The use of such treated types of cellulose causes the resulting ethanol to be uneconomical for general industrial use.

A third problem is that sugar solutions from saccharification of cellulose tend to be dilute solutions with glucose content of 5% or less, and the fermentation of such solutions leads to an ethanol concentration of about 2.4%, which is too dilute for economical purification in a distillation column. Economic distillation normally requires an incoming ethanol concentration of at least 5% or more. The cellulose concentration in the saccharification reaction is limited to concentrations which can be readily stirred, and this is typically in the range of 6 to 10% solids, although high-solids acid hydrolysis is under development. The normal corrective action is to concentrate the glucose solution by evaporation prior to the fermentation step, but this consumes unacceptable quantities of energy.

There have been many proposals to eliminate the various problems, such as aforementioned. U.S. Pat. Nos. 3,990,944, 4,094,742 and my earlier issued patent, 4,009,075, describe the use of simultaneous saccharification and fermentation for the purpose of removing the inhibiting sugars as they are formed by continually converting them to ethanol. Ethanol is not a serious inhibitor to saccharification, and satisfactory enzymatic saccharification in the presence of ethanol concentrations up to 10% has been reported by Blotkamp et al, "Enzymatic Hydrolysis of Cellulose and Simultaneous Fermentation to Alcohol", A.I.Ch.E. Symp. Series Vol. 74, No. 181, 85–90, (1978). In the process for the enzymatic conversion of cellulosic materials to sugar, as described in the patent of Wilke et al, 3,972,775, a saccharification system is disclosed in which sugars are washed from withdrawn unreacted material and the unreacted material is subsequently returned to the saccharification vessel for more reaction, while additional new cellulose is continuously added to the saccharification vessel. The process produces sugars rather than ethanol. Moreover, no recycling of ethanol-containing liquors from the fermentation reaction back into the saccharification reaction is provided. This is an important step of my present process, and which results in obtaining an increased ethanol concentration in the liquid being sent to the beer still. This increase in ethanol concentration is not achieved without the recycling treatment described.

The process of my invention produces ethanol at a lower cost than heretofore, and provides a solution to the long unsolved problem of attaining sufficiently high ethanol concentrations in the feed to the distillation column. Below 5 to 6% ethanol in the distillation column liquid raises the cost of recovering ethanol. I have discovered, however, that by using an ethanol-containing beer as a recycled diluent in the hydrolysis reaction step, in accordance with the process of this invention, the ethanol content in the feed to the distillation column can be maintained substantially above 6%. This results in producing ethanol at greatly lower cost and with less energy usage than otherwise possible.

OBJECTIVES OF THE INVENTION

The objective of this invention is to provide a process in which the saccharification and the fermentation take place in separate vessels, each at approximately atmospheric pressure and without the use of vacuum fermentation of vacuum distillation; each vessel being maintained at the optimum temperature for the reaction in that vessel.

A further objective is to recycle and reuse the saccharifying enzyme within the process, so as to greatly reduce the enzyme cost, and to accomplish this without the need for expensive separation techniques.

A further objective is to produce an alcohol-containing beer which is recycled as a diluent in the hydrolysis step, and which also forms the feed for the distillation column, and which beer contains an ethanol concentration of at least five to nine percent by weight.

A further objective is to achieve either a semi-continuous or batch-type process which is commercially practical with differing and varying cellulose-containing raw materials and which has an increased ethanol content in the feed to the distillation column.

A further objective is to have all reactions take place in low viscosity slurries which are readily stirrable, such as, for example, a six percent fiber slurry.

A further objective of the invention is to provide an improved process for making ethanol whereby provision is made for recycling ethanol-containing beer from the fermentation reaction to the saccharification reaction where the ethanol-containing beer is used as a diluent for incoming cellulosic material, thus furnishing a mixture of sugars and ethanol to the fermentation reaction to thereby increase the ethanol concentration in the feed to the ethanol purification process and lower the cost of producing ethanol.

A further objective is to withdraw unreacted raw materials from the process in a form suitable for use as boiler fuel which would furnish the process steam and the electrical power required by the process.

A still further objective is to provide a high-quality liquid motor fuel which could be used in conventional engines with 5 to 15% water content in the absence of gasoline, or which could be dehydrated and mixed with gasoline to form mixtures of ethanol and gasoline in any proportion. Such ethanol-containing fuels conserve petroleum oil which is costly and of limited supply.

The essential features of my process, as outlined by the Flow Sheet drawing, comprise the following:

(a) Forming a slurry of defibered cellulosic material by mechanically defibering the cellulosic material with beer which is recycled from the fermentation reactor, said beer containing ethanol and saccharifying enzyme;

(b) Subjecting the slurry mass to saccharification with recycles enzyme supplemented by newly added enzyme;

(c) Subjecting the saccharified slurry mass, containing sugars, ethanol, saccharifying enzyme and unreactive materials, to fermentation by yeasts;

(d) Recycling of the ethanol-containing beer from the fermentation vessel back to the saccharification reaction mass, which results in increasing the ethanol concentration in the feed liquid which is ultimately passed to a distillation column for the recovery of ethanol;

(e) The entire process being carried out under substantially atmospheric pressure conditions and without vacuum treatment.

SUMMARY OF THE INVENTION

The invention is a bioconversion process involving saccharification and fermentation, carried separately and sequentially. The incoming cellulose-containing material enters the process at a solids content of about 20% or higher, under which conditions the cellulose acts as a non-flowing solid material rather than as a flowable slurry. This cellulose mass is diluted to a stirrable solids content by admixing thereunto ethanol-containing beer recycled from the fermentation reaction, such recycled slurry also contains active saccharifying enzyme and a major fraction of the previously unreacted cellulosic raw material. The recycling of the ethanol-containing beer from the fermentation vessel back to the fermentation vessel likewise recycles the enzyme and leads to an increase in the ethanol concentration in the feed to the distillation step which otherwise is not achieved.

The saccharification is conducted at its optimum temperature and fresh cellulose-containing material is added continually to the saccharification reaction. Saccharifying enzyme is added to the saccharification chamber as needed.

The reaction mass is cooled as it enters the fermentation vessel, and where necessary an additional cooling system is provided to obtain further cooling as needed to maintain the optimum temperature for the yeast, or other microorganism used to produce the ethanol. The yeasts are added to the fermentation vessel, as necessary.

The major fraction of the reaction mass in the fermentation vessel is recirculated back to the saccharification treatment whereas a minor fraction is filtered, with the filtrate becoming the feed to the distillation tower. The filter cake is washed and pressed to make a boiler fuel, with the ethanol-containing wash water being recycled back to the saccharification reaction step.

DETAILS OF THE INVENTION AND THE PREFERRED EMBODIMENTS

A flow sheet of the process of the invention is shown to better illustrate the various steps.

The parts and percentages given throughout this application are by weight unless otherwise stated.

The design of the cellulose preparation system 1, referring to the flow sheet drawing, depends on the raw material used. If the cellulose is municipal solid waste, the system would be designed to extract a cellulosic fraction consisting of 20% to 50% of the total dry weight. If the incoming material is virgin biomass, the system 1 preferably would utilize all the incoming material. The objective of 1 is to provide a defibered cellulose, or a material which can be easily defibered subsequently in mix chamber 3, and to carry out any needed chemical prepreatment or sterilization, e.g. with steam at 212° to 270° F. If the cellulose in 1 is a wet slurry, the system would include an appropriate cone press or screw press to obtain a high solids content in the range of 20% or higher, and preferably upwards of 40%.

The cellulose enters mix chamber 3 through line 2, and is mixed with recycled slurry from line 15 and wash water from line 24. Chamber 3 is equipped with sufficient agitation to obtain a uniformly defibered slurry. Steam is added through line 4 to adjust the temperature in 3 to the optimum saccharification temperature, although the need for steam depends on the relative flows and temperatures of materials entering 3 from 2, 15 and 24. Where saccharification is accomplished by the enzyme from *Trichoderma viride*, the temperature in 3 would be adjusted to about 122° F. The enzymatic saccharification should take place at the optimum temperature for that saccharification, which usually is about 50° C. or 122° F. The mix chamber 3 functions as a high-agitation co-action section of the saccharification vessel 6. The mixing in 3 is used to insure that 6 is fed a uniform slurry of proper stirrable viscosity and temperature.

The reaction mass enters saccharification vessel 6 through line 5. Vessel 6 is designed to provide a residence time of 8 to 24 hours, or as is needed. The saccharifying agents and any needed nutrients or chemicals are added through line 7. The steam flow entering the system through line 4 is adjusted to maintain vessel 6 at its optimum temperature. Where necessary, cooling facilities may also be added to 6. The saccharified mixture in 6 passes through line 8 to heat exchanger 9, where the reaction mixture is indirectly cooled by cold water 10, which exits as warm water 11. The reaction mass is cooled sufficiently to maintain an optimum temperature for ethanol formation in fermentation vessel 13. Where ethanol is formed in 13 by use of the yeast *Saccharomyces cerevisiae*, the cooling in 9 should permit the temperature in 13 to be maintained in about the range of 77° F. to 95° F. The resultant cooled reaction mass from 9 enters the fermentation vessel 13 through line 12. Recycling of the reaction mass in 13 back through the heat exchanger 9 is an optional feature where desired.

Yeast and nutrients or chemicals are added to the fermentation vessel 13 through line 14. Carbon dioxide produced during the fermentation reaction is vented to atmosphere through line 16, with or without provision for condensing admixed ethanol vapors. The fermentation should take place at the optimum temperature for that reaction, usually about 28° C. to 33° C., or 83° F. to 91° F. A portion of the ethanol-containing beer, containing active enzyme and unreactive cellulosic materials, is recirculated from 13 back to 3 and 6 through line 15. The remainder of the reaction slurry is passed through line 17 to a filter 18, and producing a filtrate comprising a dilute beer solution which is essentially fiber-free, and which is then fed to the distillation column through line 19, from which distillation column ethanol is recovered. The unreacted dregs form a filter cake which is transported by a suitable conveyor 21 to the dregs system 22. In 22 the dregs are washed with wash water from line 23 and mechanically pressed to a solids content of about 40% or greater. The dewatered dregs are then sent to a boiler by means of conveyor 25, where they are used a fuel. The expressed wash water from 22 is returned to 3 by line 24.

The addition of wash water through line 23 is desirable but it is not essential to the process. Washing of the dregs in 22 is beneficial, however, because it reduces the concentration of ethanol in the non-solids fraction of the flow of fuel 25. If the wash water is eliminated there would be a greater loss of ethanol through 25, but this would also permit cellulose entering the process through 2 to have a lower solids content. Further, where the incoming cellulose raw material contains a high percentage of unreactive material, the slurry recycled from 13 to 3 through line 15 would retain a high viscosity and the viscosity in vessels 3 and 6 might get too high. This, however, may be remedied by diverting a portion of the slurry in line 15 through filter 18 for the purpose of removing some of the dregs in line 15.

EXAMPLES OF THE INVENTION

Operation of the process as described in the following examples is intended to be merely illustrative of the invention, and is not to be regarded as limited thereto except as set out in the claims.

EXAMPLE I

In this example a low-grade cellulosic starting material is used which is only capable of yielding 91 pounds of ethanol for 550 pounds of cellulosic material, for a yield of 16.5%. In this example, all quantities are listed as pounds per unspecified time unit, and is based on the following chemical reactions. The saccharification converts 550 pounds of cellulosic fiber into 198 pounds of sugars plus 352 pounds of dregs. The sugar is converted into 91 pounds of ethanol, 87 pounds of carbon dioxide gas and 20 pounds of other solubles.

This example can best be followed with reference to the flow sheet drawing and the numbers identifying specific parts of the process.

An incoming 550 pounds of the low-grade cellulosic material, e.g. a paper-containing fraction extracted from municipal solid waste, is defibered in 1 and is then dewatered by a belt filter followed by a cone press to achieve a solids content of approximately 45%. At that solids content the cellulose exists as a moist solid, and it is then mechanically broken up into particles of about one-half inch diameter and then fed into a continuous sterilizer wherein it is sterilized by direct steam which is added to maintain a pressure of 40 psi for ten minutes. The hot material is then flash cooled to 212° F., tne resulting solids content of the mixture approximating 42%. A conveyor-feeder unit meters the cellulose into the mix chamber 3 where it is diluted with the recycled flow from line 15. This recycled flow consists of approximately 4,911 pounds of water plus 313 pounds of ethanol plus recycled dregs, all at a temperature of 91° F. Additional dilution water is concurrently added from line 24 consisting of 1,727 pounds of water and 81 pounds of ethanol at a temperature of 80° F.

The mix chamber 3 contains an agitator with capability of reslurrying the fiberous mass. Retention time of the slurry mass in the mix chamber is one hour. The mix chamber 3 contains steam coils for indirect steam heating to thereby heat to 122° F., through use of approximately 140 pounds of low pressure steam. The material is then fed from the mix chamber 3 through line 5 to the saccharification vessel 6. The flow through line 5. The flow through line 5 consists of 7,398 pounds of water plus 550 pounds of fiber plus 394 pounds of ethanol plus some additional recycled dregs.

The retention time in the saccharification vessel 6 is 24 hours, and the primary saccharification agent is cellulase, the enzyme which attacks cellulose. A cellulase enzyme culture broth, such as prepared by the action of *Trichoderma viride* on cellulose, along with 200 pounds of water, is added to 6 through line 7. The flow through exit line 8 consists of 7,598 pounds of water plus 198 pounds of sugars plus 394 pounds of ethanol plus 352 pounds of newly-formed dregs plus some additional recycled dregs. This mixture passes through heat exchanger 9 where 293,700 BTU's are extracted and the material is thereby cooled to 83° F., and this cooled reaction mass is then fed into fermentation vessel 13 which has mild agitation. The retention time in 13 is 8 hours. Yeasts and other nutrients are added through line 14. The material flowing through line 17 to the filter 18 consists of 2,687 pounds of water plus 172 pounds of ethanol plus 352 pounds of dregs. The temperature of the fermentating mass has increased to 91° F. from the heat of fermentation, and when filtered produces a filtrate consisting of 1,363 pounds of water plus 87 pounds of ethanol. The resultant ethanol concentration of the filtrate is 6.0% by weight and 7.5% by volume. This filtrate then passes from filter 18 through line 19 and is fed to the distillation column 20 for the recovery of ethanol.

The filter cake from the filter 18 consists of 352 pounds of dregs plus 1,324 pounds of water and 85 pounds of ethanol. This is first pressed to a solids content of about 48% and then the material is mechanically shredded and washed stepwise with 928 pounds of water and again pressed to give a filter cake containing 352 pounds of dregs plus 524 pounds of water plus 4 pounds of ethanol. The filter cake has a fuel value of approximately 2,100,000 BTU's. The solution pressed from the filter cake before and during the washing is combined and recycled back to the mixing chamber 3 and the saccharification vessel 6 through line 24. The filter cake is burned in a boiler which generates steam which is used for generation of electrical power and for process steam.

EXAMPLE II

Example II emphasizes how the invention is used to produce ethanol from a high-grade cellulosic starting material, such as bleached wood pulp. In this case the ethanol yield is 30%. In this example all quantities are listed as pounds per unspecified time unit, as previously explained in Example I.

Example II is based on the following chemical reactions. The saccharification converts 550 pounds of cellulosic fiber into 359 pounds of sugars plus 191 pounds of dregs. The fermentation reaction proceeds with 90% efficiency to produce 165 pounds of ethanol plus 158 pounds of carbon dioxide plus 36 pounds of other solubles.

This example, likewise as Example I, can be followed with reference to the flow sheet drawing, the numbers identifying specific parts of the process being the same as in FIG. 1.

The incoming 550 pounds of bleached wood pulp is defibered in 1 and is then dewatered by a belt filter followed by a mechanical press to achieve a solids content of about 45%. At that solids content the cellulose exists as a moist solid, and it is then mechanically broken up into particles of about one-half inch diameter and fed into a continuous sterilizer where direct steam is added to maintain a pressure of 40 psi for ten minutes. The hot material is then flash cooled to 212° F., and the resulting solids content is 42%. A conveyor-feeder unit meters the cellulose into the mix chamber 3 where it is diluted with the flow from line 15 consisting of 4,132 pounds of water plus 409 pounds ethanol, all at a temperature of 91° F. Additional dilution water is concurrently added from line 24 consisting of 1,470 pounds of water plus 75 pounds of ethanol at a temperature of 80° F.

The mix chamber 3 contains an agitator with capability of reslurrying the cellulosic material, and the retention time in the mix chamber is about 30 minutes. The mix chamber also contains steam coils for indirect steam heating, and the mixture in 3 is heated to 122° F. through use of about 115 pounds of low pressure steam. The contents of the mix chamber 3 are then pumped through line 5 to the saccharification vessel 6. The flow through line 5 consists of 6,362 pounds of water plus 550 pounds of cellulosic fiber plus 484 pounds of ethanol plus additional recycled dregs.

The retention time in 6 is 18 hours. The primary saccharification agent is cellulase, as used in Example I, the agent which attacks cellulose. This enzyme is fortified with other enzymes such as cellobiase. The enzymes and nutrients, along with 200 pounds of water, are added through line 7. The flow from the saccharification vessel through line 8 consists of 6,562 pounds of water plus 359 pounds of sugars plus 484 pounds of ethanol plus 191 pounds of newly formed dregs plus additional recycled dregs. The mixture passes through heat exchanger 9 where it is cooled to 83° F.

The cooled material is then fed into fermentation vessel 13 which has mild agitation. The retention time in 13 is six hours. Yeasts and nutrients are added through line 14. The temperature in this vessel 13 is held at 91° F. and this is achieved by recirculating slurry from vessel 13 back through the heat exchanger 9 through a line which is not shown in the flow sheet. If a calculation of the ethanol concentration is made, based only on ethanol and water, the weight concentration of ethanol in line 8 is 6.9% and the weight concentration of ethanol in line 17 is 9.0%.

The material is fed from the fermentation vessel through line 17 to filter 18. The flow consists of 2,430 pounds of water plus 240 pounds of ethanol plus 191 pounds of dregs. The filter 18 produces a filtrate consisting of 1,638 pounds of water plus 162 pounds of ethanol, in which the ethanol concentration is 9.0% by weight and 11.2% by volume. The filtrate passes through line 19 and is fed to the distillation column 20 and recovery of ethanol.

The filter cake from the filter 18 consists of 191 pounds of dregs plus 792 pounds of water plus 78 pounds of ethanol. This is first pressed to a solids content of about 48% and then the material is mechanically shredded and washed stepwise with 961 pounds of water and again pressed to give a filter cake containing 191 pounds of dregs plus 283 pounds of water plus 3 pounds of ethanol. The filter cake has a fuel value of about 1,146,000 BTU's. The solution pressed from the filter cake before and during the washing is combined and recycled back to the mixing chamber 3 through line 24, as illustrated on the flow sheet drawing. The filter cake is burned in a boiler for the purposes of generating steam and electrical power, as heretofore mentioned.

Various microbiological agents and mixtures of such materials can be used as saccharifying agents to form sugars from incoming raw materials in accordance with the process of this invention. If the incoming cellulosic material contains almost no starchy material the saccharifying agent would be cellulase enzyme containing cellobiase activity. Further, where the incoming cellulosic material contains starchy impurities, e.g. such as in garbage, or if it contains a mixture of starch and cellulose, e.g. such as in manioc root, it is preferable to include small quantities of alpha-amylase and glucoamylase enzymes which are commonly used in the processing of corn starches. Where the starting cellulosic material is woody material with a high lignin content, it is desirable to include lignin-attacking agents such as the pleitropic mutants of wood-rotting fungus *Polyporus adustus*. This feature is described in the Canadian Journal of Microbiology, 20, (1974) p. 371-8.

Various pre-treatments of the cellulosic materials obviously may be incorporated into the cellulose preparation system 1 for the purpose of making the cellulosic materials more reactive. Such pre-treatments may include swelling with alkaline materials, acid treatments and irradiation. Further, it is apparent that persons skilled in the art will perceive that the invention can be readily modified to achieve the objectives of the invention, and which is intended to be protected by the claims hereinafter set out.

What is claimed is:

1. A continuous process for the production of ethanol, useful as a fuel, from cellulosic-containing materials which comprises the steps of:
   (a) forming a slurry mass of cellulosic material by mechanically defibering said material in a liquid mixture comprising recycled ethanol-containing beer;
   (b) subjecting said slurry mass to saccharification reaction in the presence of enzyme to form fermentable sugars from the mixture;
   (c) subjecting said fermentable sugar mixture at a suitable temperature to fermentation reaction with added yeast to produce an ethanol-containing beer; said beer additionally containing unreactive cellulosic materials;

(d) separating a portion of the ethanol-containing solution and dregs;

(e) recycling a portion of the product of step (c) back through said saccharification step and fermentation reaction step; and (f) subjecting the product resulting from step (e) to distillation to recover ethanol whereby the concentration of ethanol during fermentation and subsequent distillation treatment is substantially increased and the recovery of ethanol enhanced.

2. The process as defined in claim 1 wherein the entire process is carried out under normal atmospheric conditions and without vacuum treatment.

3. A process as defined in claim 1 wherein a major fraction of the reaction mass during the fermentation treatment is recirculated back to the saccharification treatment and a minor fraction is subjected to filtration prior to the filtrate being subjected to distillation to recover ethanol.

4. The process as defined in claim 1 in which incoming cellulose containing material comprise a solids content of over 20% and is diluted with said recycled ethanol-containing beer having an ethanol concentration of at least 2% by weight.

5. The process as defined in claim 1 in which 50% or more of the outflow from the fermentation treatment is used as a diluent for incoming cellulose-containing material.

6. A process as defined in claim 1 wherein a portion of the fermentation reaction material is subjected to filtering and a dreg system to produce a solid fuel.

7. A process as defined in claim 6 wherein the filtrate from said dreg system is returned to the mixing and saccharification treatment of cellulose-containing material being processed.

8. A process as defined in claim 6 wherein the filter from the dreg system is washed and pressed to provide a boiler fuel.

* * * * *